United States Patent
Tomioka et al.

[11] Patent Number: 5,840,741
[45] Date of Patent: Nov. 24, 1998

[54] ARTERIOSCLEROSIS DEPRESSANT

[75] Inventors: Hisao Tomioka, Ichikawa; Hidefumi Ohsawa, Narasino; Masao Moroi; Toshio Kawashima, both of Tokyo, all of Japan

[73] Assignee: Tokyo Tanabe Company Limited, Tokyo, Japan

[21] Appl. No.: 737,680
[22] PCT Filed: Feb. 24, 1995
[86] PCT No.: PCT/JP95/00277
  § 371 Date: Nov. 22, 1996
  § 102(e) Date: Nov. 22, 1996
[87] PCT Pub. No.: WO95/32714
  PCT Pub. Date: Dec. 7, 1995

[30] Foreign Application Priority Data

May 31, 1994 [JP] Japan ................................ 6-119146

[51] Int. Cl.$^6$ .................................................. A61K 31/41
[52] U.S. Cl. ............................................................ 514/381
[58] Field of Search ............................................. 514/381

[56] References Cited

FOREIGN PATENT DOCUMENTS 54-36284  3/1979  Japan .

OTHER PUBLICATIONS

Ross, The Pathogenesis of Atherosclerosis–an Update, N. Engl. J. Med., 314, 488–500 (1986).
Gyires, et al., The effect of some anti–ulcer agants on the vascular injury of gastovic mucosa induced by ethanol in rats, Acta Physio. Hung., 73 (2–3), (1989), pp. 149–154.
Definition of Arteriosclerosis, Hirokawa Pharmaceutics Dictionary $2^{nd}$ edition, p. 971.
Ross, et al., The Pathogenesis of Atherosclerosis, N. Engl. J. Med., 295, 369–377 (1976).
Ross, et al., The Pathogenesis of Atherosclerosis, N. Engl. J. Med., 295, 420–425 (1976).

*Primary Examiner*—Theodore J. Criares
*Attorney, Agent, or Firm*—Griffin, Butler, Whisenhunt & Kurtossy

[57] ABSTRACT

9-methyl-3-(1H-tetrazol-5-yl)-4H-pyrido[1, 2-a]pyrimidin-4-one represented by the following formula;

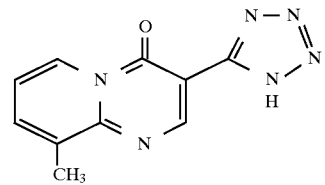

and the physiologically-acceptable salts thereof showed to have excellent inhibitory effect on the proliferation of vascular smooth muscle cells and are effective to prevent the occurrence of restenosis after the operation of PTCA, and hence the compounds can be useful for the therapeutic and preventive treatment for arteriosclerosis and other diseases whereto the proliferation of vascular smooth muscle cells is directly concerned.

9 Claims, No Drawings

ARTERIOSCLEROSIS DEPRESSANT

This is a Section 371 Application of PCT/JP95/00277 filed Feb. 24, 1995, which was a filing of Japan Application 6-119146 filed May 31, 1994.

FIELD OF THE INVENTION

The present invention is directed to a remedy for inhibiting arteriosclerosis containing 9-methyl-3-(1H-tetrazol-5-yl)-4H-pyrido[1,2-a]pyrimidin-4-one or the physiologically-acceptable salt thereof as an active component.

BACKGROUND ART

Arteriosclerosis is defined in general as a physical state in which arterial wall locally thickness and deposition of lipids and calcium salts on the thickened-parts of arterial wall takes place, whereby the elastic fibers of the vascular wall are destroyed and hence the elasticity of blood vessel is lost (see Yakukagaku Daijiten, 2nd Edition, Hirokawa Shoten, 1990), Arteriosclerosis is considered to be the cause of various diseases. Until today, clofibrates, such as clofibrate, simfibrate and alufibrate, Nicotinic acids, such as nicomol and tocopherol nicotinate, dextran sulfate esters, pantetin, cytosterol-based preparations such as soysterol, anabolic steroids, such as furazabol and oxandrolone, elastase, pravastatin and the like have been developed as therapeutic remedy for arteriosclerosis, however, there have been no remedies which have shown sufficient therapeutic effect.

It Is reported as follows concerning the mechanism of the proliferation and thickening of arterial wall. Various factors are known which cause the degeneration and ablation of endothelium cells of the arterial wall. Once such degeneration and ablation of endothelium cells is caused, platelets tend to attach to the tissues formed under the endothelium cells coagulate, then an accelerating factor for the proliferation of vascular smooth muscle cells is released from alpha-granules. Consequently, the smooth muscle cells migrate toward the intra of the arterial wall and then proliferate there to cause the thickening of the arterial wall. (See Ross, R., Glomset, J. A. :The pathogenesis of atherosclerosis, N. Engl. J. Med., 295, 369–377, 420–425, 1976. Ross, R. :The pathogenesis of atherosclerosis—an up date, N. Engl. J. Med., 314, 488–500, 1986).

Considering the mechanism described above, it is understood that remedies capable of inhibiting the proliferation of smooth muscle cells can inhibit the occurrence of arteriosclerosis as well.

Recently, a therapeutic technique called Percutaneous Transluminal Coronary Angioplasty (hereinafter referred to as PTCA) that treats narrowed blood vessels by inserting a ballon catheter into the vessels to widen them, has been widely accepted. However, restenosis of blood vessels becomes known sometime during the period 3 to 6 months after PTCA and is caused by the proliferation of smooth muscle cells. Therefore, it is understood that the inhibition of the proliferation of vascular smooth muscle cells can be an effective means to prevent the restenosis of blood vessels after PTCA.

It is an object of the present invention to provide a substance capable of inhibiting the proliferation of vascular smooth muscle cells.

SUMMARY OF THE INVENTION

The inventors of the present invention investigated substances having an inhibitory effect on the proliferation of vascular smooth muscle cells, and as a result, they found out that 9-methyl-3-(1H-tetrazol-5-yl)-4H-pyrido[1,2-a]pyrimidin-4-one (hereinafter referred to as Compound 1) and the physiologically-acceptable salts thereof, which are known to have an inhibitory effect on allergic action (see Japanese Patent Laid-opened No. Sho 54-36294 Gazette), have an inhibitory effect on the proliferation of vascular smooth muscle cells that has not been known in the past, and thereby completed the present invention.

Compound 1, an active ingredient for inhibiting arteriosclerosis of the present invention, can be obtained according to the following preparation procedure.

Firstly, ethyl 2-cyano-3-(3-methyl-2-pyridylamino)acrylate is reacted with sodium azide in the presence of aluminium chloride or the like to form a compound with a tetrazol ring. The compound is then subjected to filtration under acidic conditions to separate Compound 1. Examples of the physiologically-acceptable salts of Compound 1, are the potassium salt and the sodium salt.

The remedy for inhibiting arteriosclerosis of the present invention can be administrated orally and parenterally, and the doses of the remedy can be determined depending upon the age, symptoms, body weight and sex of the patients and other factors. In general, adequate dose per day of the active component, either Compound 1 or the salts thereof, is in a range of from 1 mg to 5 g, and more preferably from 5 mg to 1 g, for the oral administration, whereas in a range of from 0.2 mg to 1 g, and more preferably from 1 mg to 300 mg, for the parenteral administration. As to the direction for use for Compound 1 and the salt thereof, it is adequate to administer the compound 1 to 4 times per day, and more preferably once or twice per day, as far as within the dose range as specified above.

The Compound 1 and the salts thereof of the present invention can be pharmaceutically prepared into solid preparations, such as tablets, pills, capsules, powders, fine granules, granules and suppositories, or liquid preparations, such as solutions, medicated syrups, suspensions, emulsions and solutions for injection, by combining either solid or liquid physiologically-acceptable carriers with Compound 1 or the salt thereof. In the case of solid preparations, Compound 1 and the salt thereof may be prepared into enteric coated preparations and sustained release preparations. For the carriers usable for the pharmaceutical preparations of Compound 1 and the salt thereof, any carrier being commonly used for pharmaceutical preparations can be utilized, and, for examples, excipients, such as corn starch, dextrin, alpha beta- and gamma-cyclodextrins, glucose, lactose, sucrose, methyl cellulose, hydroxypropyl cellulose, carboxymethyl cellulose calcium, crystalline cellulose, sodium alginate, Witepsol W35, Witepsol E85 and polyvinyl alcohol; either binders or disintegrating agents; lubricants, such as talc, stearic acid, magnesium stearate and light anhydrous silicic acid; coating agents, such as shellac, cellulose acetate phthalate, polyvinylacetaldiethylaminoacetate, carboxymethylethyl cellulose, hydroxypropylmethyl cellulose acetate succinate, cellulose hydroxymethyl phthalate, and methylmethacrylate methacrylic acid copolymer; solution adjuvant, such as glycerin, propylene glycol and mannitol; emulsifying agents, such as polyoxyethylene stearate and polyoxyethylene lauryl alcohol ether; and suspending agents, such as acacia and polyvinylpyrrolidone, can be exemplified. In addition thereto, stabilizing agents, solvents and/or adequate perfumes may be used, if required.

DESCRIPTION OF THE PREFERRED EMBODIMENTS

Now, the inhibitory effect on the proliferation of vascular smooth muscle cells and the result of clinical test is described hereinbelow in detail, when potassium salt of Compound 1 (hereinafter referred to as Compound 1-K) is used as the representative for the remedy for Inhibiting arteriosclerosis of the present invention.

EXPERIMENTAL EXAMPLE 1

Inhibitory Effect on Deoxyribonucleic Acid (DNA) Synthesis in Vascular Smooth Muscle Cells To each well of a plate with 96 wells, cultured smooth muscle cells of aorta of a rat in an amount of 100,000 cells/well was placed, respectively. After the adhesion of the cells to the wells was made, Compound 1-K solutions in different concentrations were added to each well, respectively, and the cells were then incubated for 36 hours in Dulbecco's modified-medium added with 10% fetal calf serum. The cells were then further incubated for 2 hours in bromodeoxyuridine, then incorporation of bromodeoxyuridine into DNA was measured according to ELISA method. The rejective ratios of incorporation of bromodeoxyuridine into DNA in different concentrations of Compound 1-K solution were shown in Table 1.

TABLE 1

INHIBITORY EFFECT ON DEOXYRIBONUCLEIC ACID SYNTHESIS IN VASCULAR SMOOTH MUSCLE CELLS

|  | Concentration (M) | Ratio of incorporation of BrdU into DNA (%) |
|---|---|---|
| Control |  | 100 |
| Compound 1-K | $1 \times 10^{-8}$ | 106 |
|  | $1 \times 10^{-7}$ | 94 |
|  | $1 \times 10^{-6}$ | 86 |
|  | $1 \times 10^{-5}$ | 67 |
|  | $1 \times 10^{-4}$ | 66 |

BrdU: Bromodeoxyuridine

Compound 1-K showed concentration-dependent Inhibitory effect on DNA synthesis in the vascular smooth muscle cells at a concentration of $1 \times 10^{-7}$(M) or higher.

EXPERIMENTAL EXAMPLE 2

Inhibitory Effect on Proliferation of Vascular Smooth Muscle Cells

To each well of a plate with 6 wells, cultured smooth muscle cells of aorta of a rat in an amount of 100,000 cells/well was placed, respectively. After the reaching of the cells to sub-confluent condition, Compound 1-K solutions in different concentrations were added to each well, respectively, then the cells were incubated for 48 hours in Dulbecco's modified-medium added with 10% fetal calf serum. The number of the cells per each well was then counted. The number of the cells per well are shown in Table 2.

TABLE 2

INHIBITION EFFECT ON PROLIFERATION OF VASCULAR SMOOTH MUSCLE CELLS

| Concentration (M) |  | Number of Cells ($\times 10^4$/well) |
|---|---|---|
| Control |  | 33.5 |
| Compound 1-K | $1 \times 10^{-7}$ | 29.8 |
|  | $1 \times 10^{-4}$ | 27.8 |
|  | $1 \times 10^{-5}$ | 19.8 |
|  | $1 \times 10^{-4}$ | 17.8 |

Compound 1-K showed inhibitory effect on the proliferation of vascular smooth muscle cells at a concentration of $1 \times 10^{-7}$(M) or higher.

EXPERIMENTAL EXAMPLE 3

Clinical Tests

Patients with first elective PTCA were separated at random into a group to receive the administration of Compound 1-K (P-group: 26 patients, 39 lesions) and a group having no administration of Compound 1-K (C-group: 25 patients, 31 lesions) to carry out random comparison tests.

Compound 1-K in an amount of 20 mg/day was continuously administrated to the patients in a period from 2 weeks before the operation of PTCA till follow-up angiography, which was carried out in average at 4 months after the operation of PTCA. To all patients in the both groups described above, 81 mg of aspirin, calcium antagonist and nitrates drug were also administrated, respectively. The % stenosis was measured by using video densitometry analyser (Manufactured by PADL), and the case gained more than 20% reduction in % stenosis and less than 50% of remaining-% stenosis is defined as successful PTCA, whereas the case lost more than 50% of the gain obtained by PTCA or showed more than 50% of remaining-% stenosis is defined as restenosis. It should be noted that no difference in ratio on the sexes, age, coronary risk factors, symptom types of angina pectoris, member of diseased vessels and background of coronary artery disease was recognized between P-group and C-group. The results are shown in Table 3.

TABLE 3

CHANGE OF % CORONARY STENOSIS AND RESTENOSIS RATE

|  | P-Group | C-Group |
|---|---|---|
| % Stenosis before PTCA (%) | 77.6 ± 11.7 | 72.7 ± 8.7 |
| % Stenosis after PTCA (%) | 19.7 ± 11.2 | 21.5 ± 10.4 |
| % Stenosis at Follow-up (%) | 29.6 ± 21.0 | 46.8 ± 22.3 |
| Restenosis Rate (%) | 12.8%* | 43.9% |

*$p < 0.01$

It was confirmed that Compound 1-K has preventive effect on coronary restenosis.

Now, it is explained hereinbelow about the pharmaceutical preparation for Compound 1-K.

EXAMPLE 1

Preparation of Tablets 10.0% by weight of Compound 1-K, 56.0% by weight of lactose, 15.0% by weight of corn starch, 15.0% by weight of crystalline cellulose and 3.0% by weight of hydroxypropyl cellulose were mixed together, and the mixture was then subjected to granulation with adding water and subsequently dried.

After shaping the granules obtained, magnesium stearate in an amount of 1.0% by weight was further added to the granules and mixed, then the mixture was subjected to shaping under compression to prepare 100 mg/tablet weight of tablets.

EXAMPLE 2

Preparation of Capsules

According to a customary procedure, 10.0% by weight of Compound 1-K, 65.5% by weight of lactose, 20.0% by weight of corn starch, 3.0% by weight of hydroxypropyl cellulose, 0.5% by weight of light anhydrous silicic acid and 1.0% by weight of magnesium stearate were mixed together, and the mixture was then subjected to granulation to form into the granules. The granules obtained were charged into capsules to prepared 100 mg/capsule weight of capsules.

EXAMPLE 3

Preparation of Granules 10.0% by weight of Compound 1-K, 73.0% by weight of lactose, 10.0% by weight of low substituted hydroxypropyl cellulose, 5.0% by weight of polyvinyl pyrrolidone and 2.0% by weight of sodium lauryl sulfate were mixed together, and the mixture was then kneaded with adding water, and subsequently prepared into granules in cylindrical shape by using a oscillating granulator.

On the basis of the property to show an inhibitory effect on the proliferation of vascular smooth muscle cells, Compound 1 and the physiologically-acceptable salts thereof of the present invention can be useful for the therapeutic remedy for arteriosclerosis whereto the proliferation of vascular smooth muscle cells is directly concerned and for restenosis after the operation of PTCA.

What is claimed is:

1. A pharmaceutical preparation containing 9-methyl-3-(1H-tetrazol-5-yl)-4H-pyrido[1, 2-a]pyrimidin-4-one represented by the following chemical formula:

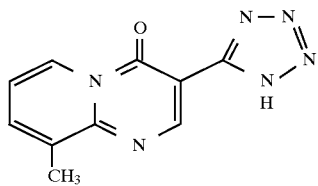

Or the physiologically-acceptable salt thereof in an effective amount to treat arteriosclerosis, and a physiologically acceptable carrier.

2. A pharmaceutical preparation according to claim 1, in solid form.

3. A pharmaceutical preparation according to claim 1, in liquid form.

4. A pharmaceutical preparation according to claim 2, wherein said solid form is suitable for oral administration.

5. A pharmaceutical preparation according to claim 3, wherein said liquid form is suitable for parenteral administration.

6. A pharmaceutical preparation according to claim 2, wherein said preparation further comprises one or more components selected from the group consisting of excipients, binders, disintegrating agents, and lubricants, and coating agents.

7. A pharmaceutical preparation according to claim 3, wherein said preparation further comprises one or more components selected from the group consisting of solution adjuvants, emulsifying agents and suspending agents.

8. A pharmaceutical preparation according to claim 6, wherein said composition is tabletted.

9. A pharmaceutical preparation according to claim 6, wherein said composition is disposed in capsules.

* * * * *